United States Patent [19]

Wiesner

[11] 4,245,997

[45] Jan. 20, 1981

[54] GAS MEASURING AND WARNING DEVICE WITH INDICATOR TUBE THROUGH WHICH GAS TO BE TESTED IS DIRECTED

[75] Inventor: Peter Wiesner, Ratekau, Fed. Rep. of Germany

[73] Assignee: Drägerwerk Aktiengesellschaft, Fed. Rep. of Germany

[21] Appl. No.: 18,871

[22] Filed: Mar. 9, 1979

[30] Foreign Application Priority Data

Apr. 6, 1978 [DE] Fed. Rep. of Germany ....... 2814843

[51] Int. Cl.³ .................... G01N 21/26; G01N 21/28; G01N 31/06
[52] U.S. Cl. .................................. 23/232 R; 422/59; 422/86; 422/91
[58] Field of Search .......................... 23/232 R, 232 E; 116/114 AM; 422/55, 59, 86, 91; 250/577

[56] References Cited

U.S. PATENT DOCUMENTS

| | | | |
|---|---|---|---|
| 4,023,930 | 5/1977 | Blunck et al. | 23/232 R |
| 4,123,227 | 10/1978 | Heim et al. | 23/232 R |

Primary Examiner—R. E. Serwin
Attorney, Agent, or Firm—McGlew and Tuttle

[57] ABSTRACT

A device and method for measuring the concentration of a gas carried in a medium such as air comprising, an indicator tube having material therein which progressively changes color along its length as it is exposed to the gas to be measured. A flow device is connected to the indicator tube for drawing or pushing the carrier with gas therethrough to cause the progressive change in color in the indicator tube material. A light barrier in the form of a light source and detector facing each other and on either side of the indicator tube is provided and mounted to slide along the axis of the indicator tube and in a direction of propagation of the progressive color change. A reference light barrier is provided in the area of the indicator tube which is not exposed to the progressive color change to produce a reference signal which is compared to a signal produced by the movable light barrier. A motor is connected to the slide mounting of the light barrier for moving it along the axis of the indicator tube and a control device is connected to the movable light barrier, the reference light barrier and the motor for maintaining the movable light barrier in the area of progressive color change which area corresponds to the concentration of the gas. An evaluator is connected to the control device for evaluating the moving position of the movable light barrier, which evaluation corresponds to the concentration of the gas. An indicator and a threshold detector may be connected in the evaluator for producing a reading corresponding to the concentration of the gas and for producing an alarm when the concentration of the gas falls below or rises above threshold values which are preselected.

10 Claims, 1 Drawing Figure

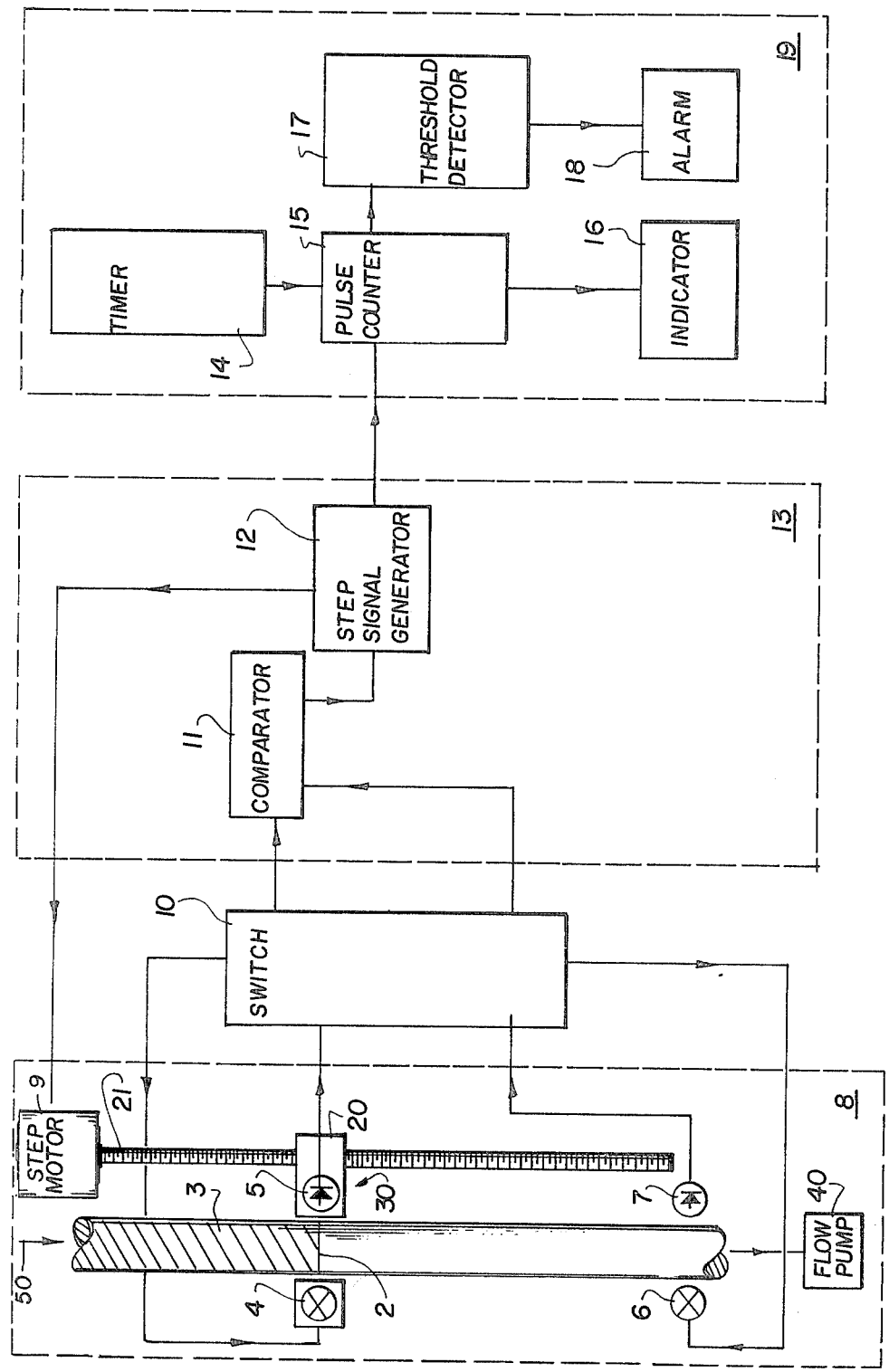

GAS MEASURING AND WARNING DEVICE WITH INDICATOR TUBE THROUGH WHICH GAS TO BE TESTED IS DIRECTED

BACKGROUND OF THE INVENTION

1. Field of the Invention

The present invention relates in general to gas detectors and, in particular, to a new and useful gas measuring and warning device which utilizes an indicator tube having material adapted to change color as the gas moves through the tube.

2. Description of the Prior Art

Indicator tubes are known which are filled with a powdery or granular chemical reagent and which generally serve the purpose of detecting gaseous components in gas mixtures which are directed through the tube by suction or pressure. During such a process, these tubes become progressively colored in the direction of the gas flow. The length of the colored zone is proportional to the amount of the gas component which had passed into the tube and to which the reagent is specifically responsive. If the quantity of the carrier gas directed through the tube by suction or pressure is known, the percentage of contamination of the carrier gas by this specific gas component can be determined from the length of the colored zone.

Such tubes are employed both for single tests and, in connection with a gas feed pump, for long-term monitoring. In either case, information is obtained on the amount of the gas to be measured that has passed into the tube. Particularly in long-term monitoring, the length of the colored zone read at the end of the monitoring period is a measure of the concentration of the gas to be measured, averaged over the entire period. In many instances, however, it is of importance to know in addition whether peaks or minima of concentration of the gas to be measured occurred some time during the monitoring period. This information can be used to instantaneously start an alarm if critical concentration values have been exceeded or not reached.

One prior art device for determining and registering certain components in the air or other gases makes it possible to determine the instantaneous concentration within shorter monitoring periods. In this device, indicator tubes accommodated in a magazine and already opened are sequentially brought into an air stream to be tested. The magazine is periodically and automatically indexed by a switching mechanism, such as a switch clock, so that a new indicator tube is always brought into the path of the air stream. The tube remains in this position until the air feeding device has passed the air through the tube under predetermined conditions.

This device is mechanically very complicated. The measured values are determined through observation and thus the reliability depends on the skill of the operator. A very disadvantageous aspect of this device is that an alarm cannot be started automatically (German Pat. No. 10 93 113).

Another prior art device for detecting gas concentrations, especially CO concentrations in the air, starts an optical and/or acoustic signal after a certain time, at a definite gas concentration indicated by the color change of the reacting layer. The device comprises a mechanically driven pump, a mount for an indicator tube at the suction side or pressure side of the pump, and a photoelectric scanner. The scanner is mounted for displacement along the indicator tube so as to scan a definite area of the indicator tube received in the mount. The intensity of the light beam from the photosensitive element of the scanner directed on the scanned area and reflected, which changes with the color of the reactive layer in the scanned area, varies the delivered current and thereby starts an optical and/or acoustic alarm. This measuring or warning device is based on the measurement of the total amount of foreign gas passing through the indicator tube and indicated by the length of the colored zone. The instantaneous concentration of the gas in the air to be tested cannot be determined. Just this quantity, however, is what is determinative. They physiologic effect of poisons depends not only on the absored amount but very strongly also on the concentration. In this respect, a measurement of the amount may even make no sense (German Offenlegungsshrift No. 15 98 021).

In still another prior art gas measuring and warning device, the monitored air is forced by pressure or suction through the indicator tube. The gas which is specific for the tube is measured, its concentration is determined and, upon exceeding certain limits, an alarm is started. To this end, the migration velocity v of the coloration front between the colored zone and the initial color is determined. This is done by means of light barriers, each comprising a light-emitting diode and a detector and light intensity of the sequentially interrogated light barriers is compared with the value recalled from a reference light barrier and converted into a yes-or-no signal. The monitoring is done in interrogation cycles and controlled by an inquiry circuit. In each cycle, a light emitting diode is sequentially triggered and the corresponding detector is interrogated. The obtained yes-signals are stored in a first counter, and the number of yes-signals from the following interrogation cycle are stored in a second counter. After each cycle resulting from the setting of the time interval, the two contents of the counters are compared with each other. The difference which is found is a measure for the velocity of migration v of the color front, and from this the gas concentration can be determined and utilized for the alarm.

In this known device, the accuracy of measurement, thus the determination of the speed of migration v of the color front, depends directly on the number of the light barriers per unit length. Therefore, to obtain a high accuracy of measurement, high costs of optical and electronic equipment must be taken into account (German Auslegungsshrift No. 26 28 790).

SUMMARY OF THE INVENTION

The present invention is directed to a device for long term monitoring which uses indicator tubes that make it possible to determine the concentration of the gases to be measured at any instant, and, upon exceeding set limiting values in both directions, to start an alarm and/or give information on the measured values.

The principal advantage obtained with the invention is measuring accuracy is substantially increased by means of a single light barrier which is very sensitively controlled and moved. The control is achieved through a spindle which is driven by a stepping motor and effected by an electronic evaluation circuit which is extremely sensitive. The light barrier is advanced by very small steps and follows the color front in an indicator tube. The number of steps per unit time, which is stored in the evaluation unit, is an exact measure of the velocity of migration of the color front and, thereby, also of the gas concentration. The employed electronic component parts are of advanced design and ensure a completely satisfactory function even over longer periods of operation.

Accordingly, an object of the present invention is to provide a device for measuring the concentration of a gas comprising an indicator tube having a material therein adapted to change color when exposed to the gas to be measured, flow means connected to said indicator tube for moving the gas into said indicator adapted to progressively change the color of the material in the tube, which progressive color change corresponds to the concentration of the gas, sensor means associated with said indicator tube adapted for sensing the progressive color change and producing a measuring signal, slide means connected to said sensor means for moving said sensor means along said indicator tube in a direction of the progressive color change, reference means associated with said indicator tube in an area thereof spaced from the progressive color change for producing a reference signal, control means connected to said sensor means, said reference means and said slide means for moving said sensor means with said slide means to maintain said sensor means in a constant relative position with respect to the progressive color change, and evaluation means connected to said control means for evaluating the movement of said sensor means.

Another object of the present invention is to provide a method for measuring the concentration of gases comprising providing an indicator tube with a material therein adapted to change color when exposed to the gas to be tested, feeding the gas to be tested into the indicator tube, providing a light sensor for sensing a progressive color change in the indicator tube, moving the light sensor along the indicator tube to maintain it in juxtaposition with the progressive color change, and evaluating the movement of the sensor tube for determining the concentration of the gas to be tested.

A still further object of the present invention is to provide a device for sensing the concentration of gases which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only drawing in the case is a block diagram and schematic representation of the device for sensing the concentration of gas in accordance with the invention.

DESCRIPTION OF THE PREFERRED EMBODIMENTS

Referring to the drawing in particular, the invention embodied therein comprises a scanning unit 8 which includes an indicator tube 1 adapted for receiving a carrier medium such as air containing a certain concentration of a gas which is supplied in the direction of arrow 50 through the use of a flow pump or vacuum pump 40 which pushes or draws the air through the tube 1. Indicator tube 1 contains a material adapted to change color progressively along the length of tube 1, which color change is specific for the gas to be tested. Control means 13 are provided for following the progressive color change in indicator tube 1, and evaluator means 19 are provided for evaluating the information supplied by the control means 30 which correspond to the position of the progressive color change.

The figure shows the gas measuring and warning device in a schematic arrangement. The gas contained in the monitored air is conducted by pressure or suction through the indicator tube which is specific for the gas. This gas is measured and its concentration is determined. If predetermined limit values are exceeded for the concentration, an alarm is started. A lower or upper limit may be set and the concentration may fall below, or rise above this limit to start the alarm.

What is measured is the velocity of migration v of the color front 2 between the changed-color zone 3 and the initial color, and this is done during the entire monitoring or measuring process. If a predetermined threshold-value of this velocity of migration v is exceeded, an alarm is started. The concentration corresponding to the just measured velocity of migration may also be indicated, in addition or even alone.

The velocity of migration v of the color front 2 is determined by a movable sensor means or measuring light barrier generally designated 30, comprising an optical transmitter 4, such as a light-emitting diode, and a detector 5. The light beam of the light barrier is directed perpendicularly to the axis of the indicator tube and through the tube 1. The intensity of the light from optical transmitter 4 is converted, by comparison with the threshold value furnished by a reference means or light barrier 6, 7 into a yes-or-no signal. This signal is determinative of further control for the movable light barrier 30.

Light barrier 30 is supported on a sliding head 20 which is guided in parallel to the axis of the indicator tube 1. Relative to the longitudinal extension of the indicator tube, optical transmitter 4 and detector 5 are positioned at the same level and on either side of the tube. Sliding head 20 is moved by means of a rotary spindle 21 and a stepping motor 9 which is controlled by a control circuit 13. Other slide mounting means may be provided to move barrier 30 above the tube axis.

The clamping and scanning unit or photoelectric scanning means 8, comprising the light barrier 30 supported on sliding head 20, and reference light barrier 6, 7, as well as stepping motor 9 with spindle 21, is connected to an electronic switch 10 and 59 a control circuit 13 which, in turn, is connected to an evaluation unit 19.

The electronic switch 10 is of conventional design and is connected to alternately switch from the light barrier 4, 5 to the reference light barrier 6, 7 and back. This prevents the two light barriers from interfering with each other. In addition, due to the modulation connected thereto, the effect of disturbing light from the outside is reduced.

Control circuit 13 comprises a comparator 11 and a step signal generator 12 which are both conventional components. Step signal generator 12 controls the stepping motor 9 by which the sliding head 20 carrying the light barrier 4, 5 is moved along the spindle. Step signal generator 12 is set into operation any time the intensity of the light determined by the light barrier 4, 5 drops below a predetermined fraction (for example 50%) of the intensity measured by reference light barrier 6, 7. As soon as the predetermined value is reached again, step signal generator 12 is stopped. Switch 10 alternately connects the two light barriers to comparator 11 to provide the two signals to be compared.

A pulse counter 15 of known design counts the number of steps of the stepping motor within a time interval which can be adjusted by means of a timer 14. If this number exceeds a value determined by a threshold-value detector 17, an optical or acoustic alarm 18 is started. The alarm threshold can be varied without mechanical means, merely by adjusting the timer 14.

The number of steps of the motor counter per time interval in pulse counter 15 and, thereby, the motion of light barrier 4, 5 are a measure of the instantaneous gas concentration to be determined. This concentration is directly displayed by an indicator 16 following pulse counter 15.

Alternate means may be provided for the step motor 9 with spindle 21 for accurately moving the sensor means 13 along tube 1. An alternate device which can be used to move the sliding head 20 is a magnetically braked balance wheel.

While specific embodiments of the invention have been shown and described in detail to illustrate the application of the principles of the invention, it will be understood that the invention may be embodied otherwise without departing from such principles.

What is claimed is:

1. A device for measuring the concentration of a gas comprising:
   an indicator tube having a material therein adapted to change color when exposed to the gas to be measured;
   flow means connected to said indicator tube for moving the gas into said indicator tube adapted to cause a progressive color change in the material in said indicator tube, which progressive color change corresponds to the concentration of the gas to be measured;
   movable sensor means associated with said indicator tube adapted for sensing the progressive color change and producing a measuring signal;
   slide means connected to said sensor means for moving said sensor means along said indicator tube in a direction of the progressive color change;
   reference means associated with said indicator tube in an area thereof spaced from the progressive color change for producing a reference signal;
   control means connected to said sensor means, said reference means and said slide means for moving said sensor means with said slide means to maintain said sensor means in a constant relative position with respect to the progressive color change; and
   evaluation means connected to said control means for evaluating the movement of said sensor means and producing a signal corresponding to the concentration of the gas to be measured.

2. A device according to claim 1 wherein said sensor means comprises a light source positioned on one side of said indicator tube and a light detector positioned on an opposite side of said sensor tube and in alignment with said light source for sensing the progressive color change in said indicator tube.

3. A device according to claim 2 wherein said reference means comprises a second light source on one side of said indicator tube and a second light detector on an opposite side of said indicator tube in alignment with said second light source.

4. A device according to claim 2 wherein said slide means comprises a sliding head for supporting said light source and said light detector, a threaded spindle threaded into said sliding head and mounted for rotation for moving said sliding head along said indicator tube when said spindle is rotated, and motor means connected to said spindle for rotating said spindle.

5. A device according to claim 4 wherein said motor means comprises a step motor.

6. A device according to claim 5 wherein said control means comprises a comparator connected to said sensor means and said reference means for comparing said measuring signal and said reference signal, and a step signal generator connected to said comparator and to said step motor for generating a step signal when the comparison of said measuring signal and said reference signal indicates that said sensor means is no longer in said constant relative position with respect to said progressive light change.

7. A device according to claim 6 further including an electric switch connected between said first-mentioned and second light detectors and said comparator for alternately connecting said first-mentioned detector and said second detector to said comparator.

8. A device according to claim 6 wherein said evaluation means comprises a pulse counter connected to said step signal generator for counting the step signals generated, a threshold connector connected to said pulse counter for producing a signal when said pulses counted rise above or fall below a selected value, an alarm connected to said threshold detector for producing an alarm when said pulses counted rise above or fall below said selected values, and an indicator connected to said pulse counter for indicating the number of pulses counted which corresponds to an instantaneous concentration of the gas to be measured.

9. A method of measuring the concentration of a gas comprising providing an indicator tube having a material therein adapted to change color when exposed to the gas to be treated and produce a progressive color change corresponding to the concentration of the gas to be tested, supplying the gas to be tested to the indicator tube for causing a progressive color change, providing a sensor for sensing the position of the progressive color change in the indicator tube, moving the sensor to maintain it in substantial alignment with the progressive color change, and evaluating the movement of the sensor to produce an indication of the movement of the sensor corresponding to an instantaneous concentration of the gas to be measured.

10. A method according to claim 9 further including producing an alarm when the concentration sensed by said evaluation falls below or rises above a selected value.

* * * * *